US00PP20136P2

(12) United States Plant Patent
Li

(10) Patent No.: US PP20,136 P2
(45) Date of Patent: Jun. 30, 2009

(54) ***VERBENA* PLANT NAMED 'KLEVP07363'**

(50) Latin Name: ***Verbena* hybrid**
Varietal Denomination: KLVP07363

(75) Inventor: Ruijun Li, North Parramata (AU)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/080,516

(22) Filed: Apr. 3, 2008

(51) Int. Cl.
*A01H 5/00* (2006.01)

(52) U.S. Cl. ..... Plt./308
(58) Field of Classification Search ..... Plt./308
See application file for complete search history.

*Primary Examiner*—S. B McCormick Ewoldt
(74) *Attorney, Agent, or Firm*—Jondle & Associates, P.C.

(57) ABSTRACT

A new cultivar of *Verbena* particularly characterized by a brilliant, large purple flower with a large eye, a mounding and healthy growth habit and good resistance to powdery mildew, is disclosed.

1 Drawing Sheet

Genus and species: *Verbena* hybrid.
Variety denomination: 'KLEVP07363'.

BACKGROUND OF THE NEW PLANT

The present invention comprises a new and distinct cultivar of *Verbena,* botanically known as *Verbena* hybrid, and hereinafter referred to by the cultivar name 'KLEVP07363'. 'KLEVP07363' was discovered as a seedling resulting from a cross conducted in fall 2004 in New South Wales, Cobbitty, Australia between the proprietary female *Verbena* parent, '00.573.20' (unpatented) and the proprietary male *Verbena* parent, '00.665.10' (unpatented). A single plant selection was subsequently chosen for further evaluation and for asexual propagation.

The new cultivar was created in fall 2004 in New South Wales, Cobbitty, Australia and has been asexually reproduced repeatedly by vegetative cuttings in Stuttgart, Germany over six generations. 'KLEVP07363' has been found to retain its distinctive characteristics through successive asexual propagations.

Plant Breeder's Rights for this cultivar were applied for in Canada on Apr. 5, 2007. 'KLEVP07363' has not been made publicly available more than one year prior to filing of this application.

SUMMARY OF THE INVENTION

The following are the most outstanding and distinguishing characteristics of this new cultivar when grown under normal commercial practices in a greenhouse in Stuttgart, Germany.

1. A brilliant, large purple flower with a large eye;
2. A mounding growth habit;
3. Good resistance to powdery mildew; and
4. Healthy growth.

DESCRIPTION OF THE PHOTOGRAPH

This new *Verbena* plant is illustrated by the accompanying photograph which shows a close-up of the mature inflorescence; the colors shown are as true as can be reasonably obtained by conventional photographic procedures. The photograph is of a plant about 4-months old and grown from rooted cuttings in an 18-cm pot under greenhouse (glasshouse) in Stuttgart, Germany under natural light.

DESCRIPTION OF THE NEW CULTIVAR

The following detailed descriptions set forth the distinctive characteristics of 'KLEVP07363'. The data which define these characteristics were collected from asexual reproductions carried out in Stuttgart, Germany. The plant history was taken on 4-month old plants in 18-cm pots grown in a glass covered greenhouse. The plants were pinched once approximately two weeks after potting. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Verbenaceae.
- *Genus and species.*—*Verbena* hybrid.
- *Common name.*—*Verbena.*

Parentage:
- *Female parent.*—The proprietary female *Verbena* plant, '00.573.20' (unpatented), having lavender flowers
- *Male parent.*—The proprietary *Verbena* plant, '00.665.10' (unpatented), having pink flowers.

Plant:
- *Plant habit.*—Mounding, use as a bedding plant or in pots.
- *Height* (*from top of soil*).—8.0 cm.
- *Width* (*horizontal plant diameter*).—25.0 cm.
- *Time to produce a finished flowering plant.*—14 weeks (from sticking of unrooted cuttings).
- *Time to initiate and develop roots.*—3 weeks.
- *Root description.*—Normal shape and texture.

Stems:
- *Number of branches per plant.*—Greater than 10.
- *Length.*—Approximately 8.0 cm.
- *Diameter* (*measured from the midpoint*).—8.0 cm.
- *Internode length.*—Approximately 1.5 cm.
- *Color.*—RHS 140C.

*Anthocyanin.*—Present. Color: RHS 140C.
*Texture.*—Pubescent.
*Shape.*—Round.

Leaves:
*Arrangement.*—Opposite.
*Immature leaf.*—Color (both surfaces): RHS 135C.
*Mature leaf.*—Color (both surfaces): RHS 135B. Length: 3.5 cm. Width: 2.0 cm.
*Shape.*—Ovate to deltoid.
*Apex.*—Cuspidate.
*Base.*—Attenuate.
*Margin.*—Crenate.
*Texture.*—Upper surface: Smooth.
*Venation.*—Pinnate.
*Venation color.*—Upper surface: RHS 135B.
*Petioles.*—Length: Less than 0.3 cm. Diameter: Less than 0.3 cm. Color RHS 140C. Texture: Pubescent.

Flower buds:
*Shape.*—Tall, cylindrical.
*Length.*—1.0 cm.
*Diameter.*—Less than 0.1 cm.
*Color* (*at tight bud*).—RHS 140C.

Inflorescence:
*Blooming habit* (*flowering season*).—Spring to fall (April to December) Lastingness of individual blooms on the plant: Approximately 3 weeks, moderate.
*Fragrance.*—Absent.
*Inflorescence shape.*—Fan shaped, simple corymbs.
*Length of inflorescence.*—2.0 cm.
*Diameter of inflorescence.*—2.0 cm.
*Number of florets per inflorescence.*—More than 25.
*Peduncle.*—Length: Approximately 2.0 cm. Diameter: Approximately less than 0.2 cm. Color: RHS 140C. Texture: Pubescent.

Florets (with white eye):
*Form.*—Radial.
*Length.*—Approximately 0.6 cm.
*Diameter.*—Approximately 1.7 cm.
*Color* (both immature and mature).—Upper surface: RHS 74A. Lower surface: RHS 74B.
*Corolla tube length.*—0.5 cm.
*Corolla tube color.*—RHS 74C.
*Petals.*—Length of lobe: Less than 0.7 cm. Diameter of lobe: Less than 0.1 cm. Lobe shape: Obovate. Apex: Obtuse. Base: Fused. Margin: Entire. Texture (both surfaces): Smooth.
*Pedicels.*—Length: Greater than 1.5 cm. Diameter: Greater than 0.1 cm. Color: RHS 74C. Texture: Smooth.

Sepals:
*Shape.*—Cylindrical.
*Length.*—Greater than 1.0 cm.
*Diameter.*—Greater than 0.2 cm.
*Color.*—RHS 135C.
*Apex.*—Cuspidate.
*Base.*—Obtuse.
*Margin.*—Crenate.
*Texture.*—Satiny.

Reproductive organs:
*Stamens.*—Quantity: 4. Shape: Too small to characterize. Color: Creamy white. Filament length: Less than 0.1 cm. Filament diameter: Less than 0.1 cm.
*Anther.*—Shape: Too small to characterize. Color: Too small to characterize. Length: Less than 0.1 cm. Diameter: Less than 0.1 cm.
*Pollen.*—Color: Too small to characterize. Amount: Too small to quantify.
*Pistils.*—Number: 1. Length: 1.0 cm. Diameter: 0.1 cm. Stigma: Color: Pale green. Shape: Round. Length: Less than 0.1 cm. Diameter: Less than 0.1 cm. Style: Color: Pale green. Length: Less than 0.1 cm. Diameter: Less than 0.1 cm. Shape: Ovate.

Fruit and seed set: None observed.

Disease and insect resistance: Good powdery mildew resistance

COMPARISON WITH PARENTAL AND COMMERCIAL CULTIVARS

'KLEVP07363' differs from the female parent, the proprietary *Verbena* '00.573.20' (unpatented) in that 'KLEVP07363' has purple flowers with a large eye, while '00.573.20' has lavender flowers.

'KLEVP07363' differs from the male parent, the proprietary *Verbena* '00.665.10' (unpatented) in that 'KLEVP07363' has purple flowers with a large eye, while '00.573.20' has pink flowers.

'KLEVP07363' differs from the commercial comparison variety 'KLEVP05344' (U.S. Plant Pat. No. 18,584) in that 'KLEVP07363' has purple flowers with a large eye, while 'KLEVE05344' has purple flowers without an eye.

I claim:

1. A new and distinct cultivar of *Verbena* plant as shown and described herein.

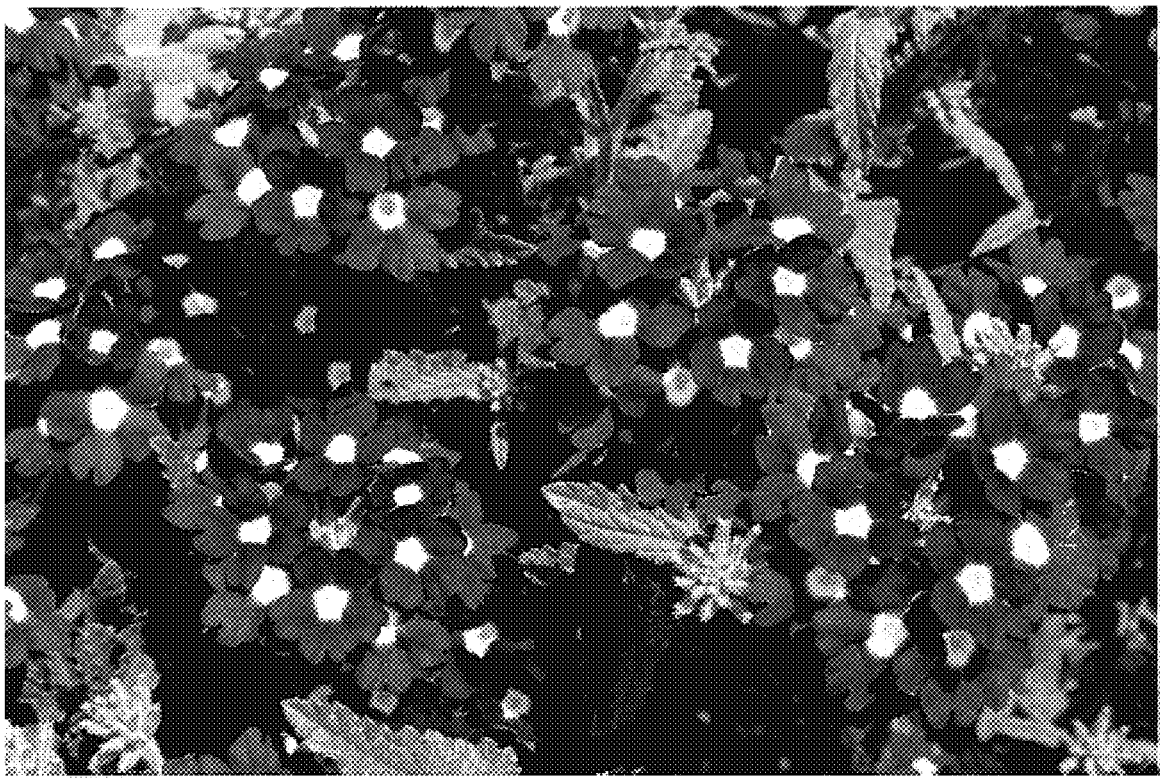

* * * * *